(12) United States Patent
Higuchi et al.

(10) Patent No.: US 10,647,638 B2
(45) Date of Patent: May 12, 2020

(54) METHOD FOR PRODUCING BUTADIENE

(71) Applicant: JXTG Nippon Oil & Energy Corporation, Chiyoda-ku, Tokyo (JP)

(72) Inventors: Sosuke Higuchi, Tokyo (JP); Nobuhiro Kimura, Tokyo (JP)

(73) Assignee: JXTG Nippon Oil & Energy Corporation, Tokyo (JP)

( * ) Notice: Subject to any disclaimer, the term of this patent is extended or adjusted under 35 U.S.C. 154(b) by 7 days.

(21) Appl. No.: 15/779,615

(22) PCT Filed: Oct. 19, 2016

(86) PCT No.: PCT/JP2016/080971
§ 371 (c)(1),
(2) Date: May 29, 2018

(87) PCT Pub. No.: WO2017/094382
PCT Pub. Date: Jun. 8, 2017

(65) Prior Publication Data
US 2018/0346395 A1    Dec. 6, 2018

(30) Foreign Application Priority Data

Dec. 1, 2015  (JP) ................................. 2015-234994

(51) Int. Cl.
| | | |
|---|---|---|
| *C07C 5/48* | (2006.01) | |
| *B01J 37/08* | (2006.01) | |
| *B01J 37/04* | (2006.01) | |
| *B01J 23/00* | (2006.01) | |
| *B01J 23/31* | (2006.01) | |
| *C07C 11/167* | (2006.01) | |
| *B01J 23/887* | (2006.01) | |

(52) U.S. Cl.
CPC .............. *C07C 5/48* (2013.01); *B01J 23/002* (2013.01); *B01J 23/31* (2013.01); *B01J 23/8876* (2013.01); *B01J 37/04* (2013.01); *B01J 37/088* (2013.01); *C07C 11/167* (2013.01); *B01J 2523/54* (2013.01); *B01J 2523/68* (2013.01); *C07C 2523/18* (2013.01); *C07C 2523/28* (2013.01); *C07C 2523/31* (2013.01); *C07C 2523/745* (2013.01); *C07C 2523/75* (2013.01); *C07C 2523/887* (2013.01)

(58) Field of Classification Search
None
See application file for complete search history.

(56) References Cited

U.S. PATENT DOCUMENTS

2012/0130137 A1* 5/2012 Orita ...................... B01J 23/002
585/621

FOREIGN PATENT DOCUMENTS

| | | |
|---|---|---|
| JP | S60-115532 A | 6/1985 |
| JP | S60-126235 A | 7/1985 |
| JP | 2003-220335 A | 8/2003 |
| JP | 2011-006381 A | 1/2011 |
| JP | 2012-077076 A | 4/2012 |
| JP | 2012-106942 A | 6/2012 |
| JP | 2012-111699 A | 6/2012 |
| WO | WO 2010/137595 A1 | 12/2010 |
| WO | WO 2012/157495 A1 | 11/2012 |

OTHER PUBLICATIONS

Japan Patent Office, International Search Report issued in International Application No. PCT/JP2016/080971 (dated Jan. 10, 2017).
International Bureau of WIPO, International Preliminary Report on Patentability and Written Opinion issued in International Application No. PCT/JP2016/080971 (dated Jun. 14, 2018).
Jung et al., "Effect of calcination temperature on the catalytic performance of Co9Fe3Bi1Mo12O51 in the oxidative dehydrogenation of n-butene to 1,3-butadiene," *Catalysis communications*, 9(10): 2059-2062 (2008).

* cited by examiner

*Primary Examiner* — Ali Z Fadhel
(74) *Attorney, Agent, or Firm* — Leydig, Voit & Mayer, Ltd.

(57) ABSTRACT

A method for producing butadiene comprises a step of obtaining a product gas containing butadiene, by feeding a raw-material gas containing straight-chain butene and an oxygen-containing gas containing molecular oxygen to a reactor and performing oxidative dehydrogenation reaction in the presence of a catalyst, wherein the catalyst comprises a composite oxide containing molybdenum and bismuth, and the concentration of hydrocarbons having 5 or more carbon atoms in the raw-material gas is 0.05 mol % to 7.0 mol %.

3 Claims, No Drawings

METHOD FOR PRODUCING BUTADIENE

CROSS-REFERENCE TO RELATED APPLICATIONS

This patent application is the U.S. national phase of International Application No. PCT/JP2016/080971, filed on Oct. 19, 2016, which claims the benefit of Japanese Patent Application No. 2015-234994, filed Dec. 1, 2015, the disclosures of which are incorporated herein by reference in their entireties for all purposes.

TECHNICAL FIELD

The present invention relates to a method for producing butadiene.

BACKGROUND ART

Methods for producing butadiene by oxidative dehydrogenation reaction of straight-chain butene in the presence of a catalyst have been conventionally known (for example, Patent Literature 1 and Patent Literature 2).

In a method for producing butadiene, for example, a mixture containing straight-chain butene and butanes obtained by removing butadiene from a C4 fraction such as a C4 fraction produced as by-product by naphtha cracking, or a C4 fraction produced as by-product by fluid catalytic cracking is used as a raw material.

Furthermore, as a catalyst for such oxidative dehydrogenation reaction, for example, a composite oxide containing bismuth and molybdenum is known (for example, Patent literature 3 and Non patent literature 1).

In the meantime, the above-mentioned method for producing butadiene is known to be problematic in that a by-product resulting from oxidative dehydrogenation reaction causes reactor blockage (for example, Patent literature 4).

CITATION LIST

Patent Literature

Patent Literature 1: Japanese Unexamined Patent Publication No. S60-115532
Patent Literature 2: Japanese Unexamined Patent Publication No. S60-126235
Patent Literature 3: Japanese Unexamined Patent Publication No. 2003-220335
Patent Literature 4: Japanese Unexamined Patent Publication No. 2012-111699

Non Patent Literature

Non Patent Literature 1: Catalyst Communication, 9 (2008), 2059-2062

SUMMARY OF INVENTION

Technical Problem

An object of the present invention is to provide a method for producing butadiene by oxidative dehydrogenation reaction of straight-chain butene, which can inhibit reactor blockage, can continue stable operation for a long time, and thus is an industrially advantageous method for producing butadiene.

Solution to Problem

As a result of intensive studies to achieve the above object, the present inventors have discovered that specifying the concentration of hydrocarbons having 5 or more carbon atoms in a raw-material gas within a predetermined range makes it possible to reduce the amount of the generated solid blockage materials inhibiting the stable operation of the reactor, to continuously perform stable operation for a long time, and, to perform stable production of butadiene with high yields.

An aspect of the present invention relates to a method for producing butadiene.

In an aspect, the method for producing butadiene comprises a step of obtaining a product gas containing butadiene, by feeding a raw-material gas containing straight-chain butene and an oxygen-containing gas containing molecular oxygen to a reactor and performing oxidative dehydrogenation reaction in the presence of a catalyst. In this aspect, the catalyst comprises a composite oxide containing molybdenum and bismuth, and the concentration of hydrocarbons having 5 or more carbon atoms in the raw-material gas is 0.05 mol % to 7.0 mol %.

In an aspect, the concentration of hydrocarbons having 5 or more carbon atoms in a raw-material gas may be 0.2 mol % to 6.0 mol %.

In an aspect, the concentration of straight-chain butene in a raw-material gas may be 60 mol % or more.

Advantageous Effects of Invention

According to the present invention, a method for producing butadiene by oxidative dehydrogenation reaction of straight-chain butene, which can inhibit reactor blockage, can continue stable operation for a long time, and thus is an industrially advantageous method for producing butadiene, is provided.

DESCRIPTION OF EMBODIMENTS

Preferred embodiments of the present invention are described as follows. Note that descriptions given below are merely examples of the embodiments of the present invention, and the present invention is not limited to them.

The production method according to the embodiments comprises a step of obtaining a product gas containing butadiene, by feeding a raw-material gas containing straight-chain butene and an oxygen-containing gas containing molecular oxygen to a reactor and performing oxidative dehydrogenation reaction in the presence of a catalyst. Moreover, in the embodiments, the catalyst comprises a composite oxide containing molybdenum and bismuth, the concentration of hydrocarbons having 5 or more carbon atoms in the raw-material gas is 0.05 mol % to 7.0 mol %.

In the production method according to the embodiments, reactor blockage is inhibited sufficiently, and stable operation can be continued for a long time.

Conventional methods for producing butadiene are problematic in that in a subsequent stage of a reactor, a by-product (or a polymer and the like produced because of the by-product) may be deposited to cause reactor blockage. In contrast, in the production method according to the embodiments, the raw-material gas contains a predetermined amount of hydrocarbons having 5 or more carbon atoms. Therefore, in the embodiments, it is considered that when a product gas is cooled in the subsequent stage of the reactor, hydrocarbons having 5 or more carbon atoms are liquefied by condensation to dissolve or wash away the by-product, thereby inhibiting reactor blockage. Such a mechanism of the effect exerted by the hydrocarbons having 5 or more carbon atoms is not limited to the above.

It is considered that the higher the concentration of hydrocarbons having 5 or more carbon atoms in the raw-material gas becomes, the more effects of dissolving by-products well and inhibiting reactor blockage increase. In the meantime, if the concentration is excessively high, the thus increased amount of inactive components in the raw-material gas increases the amount of energy required for heating the raw-material gas, which can lower the energy efficiency. Furthermore, if the concentration of hydrocarbons having 5 or more carbon atoms is excessively high, the concentration of straight-chain butene is lowered and the time of contact of straight-chain butene and a catalyst is shortened, which may lower the reaction efficiency. Accordingly, the concentration of hydrocarbons having 5 or more carbon atoms is desired to be within a specific range.

The concentration of hydrocarbons having 5 or more carbon atoms in the raw-material gas is preferably 0.1 mol % or more, and more preferably 0.2 mol % or more. Moreover, the concentration of hydrocarbons having 5 or more carbon atoms in the raw-material gas is preferably 6.0 mol % or less and more preferably 5.5 mol % or less.

The number of carbon atoms in the above hydrocarbons may be, for example, 25 or less, and is preferably 20 or less, and is more preferably 15 or less. Moreover, the above hydrocarbons are not particularly limited, but are preferably saturated hydrocarbons. Furthermore, the above hydrocarbons may be straight-chain, branched or cyclic, and are preferably straight-chain or branched.

The raw-material gas may contain straight-chain butene as a main component. The concentration of straight-chain butene in the raw-material gas may be, for example, 60 mol % or more, and is preferably 70 mol % or more. Furthermore, the concentration of straight-chain butene in the raw-material gas may be, for example, 99.95 mol % or less, 95 mol % or less, 90 mol % or less, and 85 mol % or less. The straight-chain butene may be either 1-butene or 2-butene, or a mixture of the two.

The raw-material gas may further contain butanes. An example of butanes is a saturated hydrocarbon having 4 carbon atoms, and may be either n-butane or isobutane, or a mixture of the two. The concentration of butanes in the raw-material gas is not particularly limited, and may be, for example, 10 mol % or more, 15 mol % or more, 40 mol % or less, and 30 mol % or less.

The concentration of isobutene in the raw-material gas is preferably low, may be, for example, 3.0 mol % or less, and preferably 1.0 mol % or less.

The concentration of butadiene in the raw-material gas is preferably low, may be, for example, 3.0 mol % or less, and is preferably 1.0 mol % or less.

The raw-material gas may be prepared by adding hydrocarbons having 5 or more carbon atoms to isolated straight-chain butene. Furthermore, the raw-material gas may be prepared by adjusting the amount of hydrocarbons having 5 or more carbon atoms to be mixed upon separation or purification of a C4 fraction containing straight-chain butene. Moreover, as the raw-material gas, for example, a fraction containing straight-chain butene and butanes obtained by separating butadiene and isobutene from a C4 fraction produced as by-product by naphtha cracking may be used. Moreover, as the raw-material gas, for example, a fraction generated by dehydrogenation reaction of n-butane may also be used. Moreover, as the raw-material gas, for example, a fraction obtained by dimerization of ethylene may also be used. Moreover, as the raw-material gas, for example, a C4 fraction may also be used, which is obtained by fluid catalytic cracking that involves breaking down a heavy oil fraction obtained by distillation of crude oil at a petroleum refining plant or the like using a powdery solid catalyst under a fluidized bed condition, and then converting the resultant to a low boiling point hydrocarbon.

In the embodiments, a reactor to be used for oxidative dehydrogenation reaction is not particularly limited. Examples of the reactor include a tube reactor, a tank reactor, and a fluid bed reactor, and the reactor is preferably a fixed bed reactor, and more preferably a fixed-bed multi-pipe reactor. These reactors may be those generally industrially used.

The oxygen-containing gas may be, for example, a gas containing 10% by volume or more of molecular oxygen, is preferably a gas containing 15% by volume or more of molecular oxygen, and is more preferably a gas containing 20% by volume or more of molecular oxygen. The oxygen-containing gas may be, for example, air. The concentration of molecular oxygen in the oxygen-containing gas may be, in view of cost reduction, 50% by volume or less, is preferably 30% by volume or less, and more preferably 25% by volume or less.

The oxygen-containing gas may contain components other than molecular oxygen, as long as the above effects are exerted. Examples of the components include nitrogen, argon, neon, helium, CO, $CO_2$, and water. The concentration of nitrogen (molecular nitrogen) in oxygen-containing gas may be, for example, 50% by volume or more, 70% by volume or more, and 75% by volume or more. Moreover, the concentration of nitrogen in the oxygen-containing gas may be, for example, 90% by volume or less, 85% by volume or less, and 80% by volume or less. The concentration of components other than nitrogen may be, for example, 10% by volume or less, and is preferably 1% by volume or less.

When the raw-material gas is fed to a reactor 1, a nitrogen gas and water (water vapor) may be fed together with the raw-material gas and the oxygen-containing gas. The nitrogen gas is fed in view of adjusting the concentrations of a combustible gas and molecular oxygen, so that a reactant gas does not form a detonating gas. Water (water vapor) is fed in a manner similar to that for the nitrogen gas, in view of adjusting the concentrations of a combustible gas and molecular oxygen and in view of inhibiting catalyst coking.

Since mixing of the raw-material gas with an oxygen-containing gas results in a mixture of a combustible gas and molecular oxygen, compositional control may be performed at the reactor inlet while monitoring the flow rate using a flowmeter installed at piping for supplying each gas (a raw-material gas, an oxygen-containing gas, and if necessary, a nitrogen gas and water (water vapor)), so that the gas composition does not fall within the range of explosion. The compositional control adjusts the composition range to be a reactant gas composition described later, for example.

Note that, the term "range of explosion" refers to a range of the composition of a mixed gas of a combustible gas and molecular oxygen, within which the mixed gas is ignited in the presence of an ignition source. When the concentration of a combustible gas is lower than a value, the gas is not ignited even in the presence of an ignition source. This concentration is referred to as a lower explosive limit. In addition, when the concentration of a combustible gas is higher than a value, the gas is not ignited similarly even in the presence of an ignition source. This concentration is referred to as an upper explosive limit. Each value depends on an oxygen concentration. In general, the lower the oxygen concentration is, the closer the two limits are, and the two limits become the same when the oxygen concentration reaches a certain value. The oxygen concentration at this time is referred to as "limiting oxygen concentration". If the oxygen concentration is lower than the limiting oxygen concentration, the mixed gas is not ignited regardless of the concentration of a combustible gas.

In the embodiments, for example, a method may be employed, which comprises initially adjusting the amounts of an oxygen-containing gas, nitrogen and water vapor shared in a reactor, so as to regulate the oxygen concentration at the reactor inlet at a limiting oxygen concentration or less, initiating the feeding of the raw-material gas, subsequently, increasing the amounts of the raw-material gas and the oxygen-containing gas to be fed to increase the concentration of a combustible gas to a level higher than the upper explosive limit, and thus initiating the reaction. Furthermore, when the amounts of the raw-material gas and the oxygen-containing gas to be fed are increased, the amounts of nitrogen and/or water vapor to be fed may be decreased to keep the amounts of the gases to be fed at certain levels. Accordingly, the gas residence time in the piping and the reactor can be maintained at certain levels and pressure fluctuation can be suppressed.

A typical reactant gas composition to be fed to a reactor is as shown below.

<Reactant Gas Composition>

Straight-chain butene: 50% by volume to 100% by volume based on the total amount of hydrocarbons having 4 carbon atoms Hydrocarbons having 4 carbon atoms: 5% by volume to 15% by volume based on the total amount of reactant gases $O_2$: 40% by volume to 120% by volume based on the total amount of hydrocarbons having 4 carbon atoms $N_2$: 500% by volume to 1000% by volume based on the total amount of hydrocarbons having 4 carbon atoms $H_2O$: 90% by volume to 900% by volume based on the total amount of hydrocarbons having 4 carbon atoms The reactor is filled with a catalyst described later, and straight-chain butene reacts with oxygen on the catalyst, generating butadiene and water. The oxidative dehydrogenation reaction is exothermic reaction by which the temperature increases. The reaction temperature is preferably adjusted within a range between 280° C. and 400° C. Therefore, the reactor is preferably capable of controlling the temperature of a catalyst layer at a certain level using a heating medium (for example, dibenzyltoluene, and nitrite).

The pressure of the reactor is not particularly limited. The pressure of the reactor is generally 0 MPaG or more, may be 0.001 MPaG or more, and 0.01 MPaG or more. A merit is that the higher the pressure of the reactor becomes, the larger the amount of reactant gases can be fed to the reactor. On the other hand, the pressure of the reactor is generally 0.5 MPaG or less, and may be 0.3 MPaG or less, and 0.1 MPaG or less. The lower the pressure of the reactor becomes, the narrower the range of explosion tends to become.

The residence time of the reactor is not particularly limited. The residence time of the reactor may be, for example, 0.1 second or more, and is preferably 0.5 second or more. An advantage is that as the value of the residence time of the reactor increases, the conversion rate of straight-chain butene due to oxidative dehydrogenation reaction is increased. In the meantime, the residence time of the reactor may be, for example, 10 seconds or less, and is preferably 5 seconds or less. The lower the value of the residence time of the reactor, the smaller the size the reactor can have.

In the embodiments, a product gas containing butadiene is obtained by oxidative dehydrogenation reaction. The concentration of butadiene in a product gas can be varied depending on the concentration of straight-chain butene in a raw-material gas, and may be, for example, 1% by volume to 15% by volume, may be 5% by volume to 13% by volume, and may also be 6% by volume to 11% by volume. If the concentration of butadiene in a product gas is high, the recovery cost can be reduced. Moreover, if the concentration of butadiene in a product gas is low, side reaction such as polymerization hardly takes place in downstream steps.

The product gas may further contain unreacted straight-chain butene. The concentration of straight-chain butene in the product gas may be, for example, 7% by volume or less, 4% by volume or less, and 2% by volume or less.

The product gas may further contain a by-product of oxidative dehydrogenation reaction. Examples of the by-product include aldehydes.

In the embodiments, the product gas further contains hydrocarbons having 5 or more carbon atoms. It is considered that the product gas containing hydrocarbons having 5 or more carbon atoms causes by-products or polymers thereof to be dissolved or washed away in the subsequent stage of the reactor, thereby inhibiting reactor blockage.

[Catalyst]

Preferred aspects of the catalyst (oxidative dehydrogenation reaction catalyst) to be used in the production method according to the embodiments are described in detail as follows.

In the embodiments, the oxidative dehydrogenation reaction catalyst may be a composite oxide catalyst containing a composite oxide that contains molybdenum and bismuth.

The composite oxide catalyst may further contain cobalt, for example.

The composite oxide catalyst may contain, for example, a composite oxide represented by the following formula (1).

$$(Mo)a(Bi)b(Co)c(Ni)d(Fe)e(X)f(Y)g(Z)h(Si)i(O)j \qquad (1)$$

(wherein X represents at least one type of element selected from the group consisting of magnesium (Mg), calcium (Ca), zinc (Zn), cerium (Ce) and samarium (Sm), Y represents at least one type of element selected from the group consisting of sodium (Na), potassium (K), rubidium (Rb), cesium (Cs) and thallium (Tl), and Z represents at least one type of element selected from the group consisting of boron (B), phosphorus (P), arsenic (As) and tungsten (W). Moreover, a to j represent the values of the atomic ratios of each element, wherein when a=12, b=0.5 to 7, c=0 to 10, d=0 to 10 (however, c+d=1 to 10), e=0.05 to 3, f=0 to 2, g=0.04 to 2, h=0 to 3, and i=0 to 48, and j is a numerical value satisfying the oxidation state of other elements.)

A method for producing the composite oxide catalyst is not particularly limited. For example, the composite oxide catalyst may be obtained by mixing supply source compounds of each constituent element in a water system and then calcining the resulting mixture.

Examples of the above supply source compound of each constituent element include an oxide, a nitrate, a carbonate, an ammonium salt, a hydroxide, a carboxylate, a carboxylic acid ammonium salt, halogenated ammonium salt, hydroacid, acetylacetonate, and alkoxide of constituent elements.

Examples of a supply source compound of Mo include ammonium paramolybdate, molybdenum trioxide, molybdic acid, ammonium phosphomolybdate, and phosphomolybdic acid.

Examples of a supply source compound of Fe include ferric nitrate, ferric sulfate, ferric chloride, and ferric acetate.

Examples of a supply source compound of Co include cobalt nitrate, cobalt sulfate, cobalt chloride, cobalt carbonate, and cobalt acetate.

Examples of a supply source compound of Ni include nickel nitrate, nickel sulfate, nickel chloride, nickel carbonate, and nickel acetate.

Examples of a supply source compound of Si include silica, granular silica, colloidal silica, and fumed silica.

Examples of a supply source compound of Bi include bismuth chloride, bismuth nitrate, bismuth oxide, and bismuth subcarbonate. The supply source compound can also be fed as a composite carbonate compound of Bi and an X component and/or a Y component, prepared by subjecting the X component (1 type or 2 or more types of Mg, Ca, Zn, Ce and Sm) and/or the Y component (1 type or 2 or more types of Na, K, Rb, Cs and Tl) to solution treatment.

For example, when Na is used as the Y component, a composite carbonate compound of Bi and Na can be produced by adding dropwise an aqueous solution of a water-soluble bismuth compound such as bismuth nitrate to and mixing the same with an aqueous solution or the like of sodium carbonate, sodium bicarbonate, and then washing with water and drying the thus obtained precipitate. Moreover, a composite carbonate compound of Bi and the X component can be produced by adding dropwise an aqueous solution consisting of a water-soluble compound such as bismuth nitrate and nitrate of the X component to and mixing the same with an aqueous solution or the like of ammonium carbonate or ammonium bicarbonate, and then washing with water and drying the thus obtained precipitate. A composite carbonate compound of Bi, and Na and the X component can be produced using sodium carbonate or sodium bicarbonate instead of ammonium carbonate or ammonium bicarbonate.

Examples of a supply source compound of K can include potassium nitrate, potassium sulfate, potassium chloride, potassium carbonate, and potassium acetate.

Examples of a supply source compound of Rb can include rubidium nitrate, rubidium sulfate, rubidium chloride, rubidium carbonate, and rubidium acetate.

Examples of a supply source compound of Cs can include cesium nitrate, cesium sulfate, cesium chloride, cesium carbonate, and cesium acetate.

Examples of a supply source compound of Tl can include thallous nitrate, thallous chloride, thallous carbonate, and thallous acetate.

Examples of a supply source compound of B can include borax, ammonium borate, and boric acid.

Examples of a supply source compound of P can include ammonium phosphomolybdate, ammonium phosphate, phosphoric acid, and phosphorus pentoxide.

Examples of a supply source compound of As can include diarseno 18 ammonium molybdate, and diarseno 18 ammonium tungstate.

Examples of a supply source compound of W can include ammonium paratungstate, tungstic trioxide, tungstic acid, and phosphotungstic acid.

Examples of a supply source compound of Mg include magnesium nitrate, magnesium sulfate, magnesium chloride, magnesium carbonate, and magnesium acetate.

Examples of a supply source compound of Ca include calcium nitrate, calcium sulfate, calcium chloride, calcium carbonate, and calcium acetate.

Examples of a supply source compound of Zn include zinc nitrate, zinc sulfate, zinc chloride, zinc carbonate, and zinc acetate.

Examples of a supply source compound of Ce include cerium nitrate, cerium sulfate, cerium chloride, cerium carbonate, and cerium acetate.

Examples of a supply source compound of Sm include samarium nitrate, samarium sulfate, samarium chloride, samarium carbonate, and samarium acetate.

A mixture prepared by mixing the supply source compounds of each constituent element in a water system may be calcined after drying. The calcination temperature is not particularly limited, may be, for example, may be 300° C. to 700° C., and may also be 400° C. to 600° C. The time for calcination is not particularly limited, and may be, for example, 1 to 12 hours, and may also be 4 to 8 hours.

The shape of the composite oxide catalyst is not particularly limited, and may be varied as appropriate depending on the form or the like of a reactor. For example, the composite oxide catalyst may be granular. When the composite oxide catalyst is granular, the particle diameter may be, for example, 0.1 mm to 10.0 mm, and may also be 1.0 mm to 5.0 mm.

Preferred embodiments of the present invention are as described above, but the present invention is not limited to the above embodiments.

EXAMPLES

The present invention will be more specifically described below by way of Examples, but the present invention is not limited to the Examples.

Production Example 1: Preparation of Composite Oxide Catalyst

Cobalt nitrate.hexahydrate (12.3 g) and 5.8 g of iron nitrate.enneahydrate were added to 25.0 g of pure water, and stirred at ordinary temperature for dissolution. The solution is designated as solution A.

Next, 1.0 g of concentrated nitric acid was added to 5.0 g of pure water to acidify the solution, and then 2.3 g of bismuth nitrate.pentahydrate was added. The solution was stirred at ordinary temperature for dissolution. The solution is designated as solution B.

Next, 10.0 g of ammonium molybdate.tetrahydrate was added to 70.0 g of pure water, and stirred at ordinary temperature for dissolution. The solution is designated as solution C.

Next, solution B was added dropwise to and mixed with solution A. The resulting solution was added dropwise to solution C, and then stirred at ordinary temperature, followed by 2 hours of mixing. The thus obtained solution was evaporated to dryness, further dried at 175° C. overnight, and then subjected to, under an air atmosphere, 5 hours of calcination at 530° C., thereby obtaining composite oxide powder. The thus obtained powder was tableted, and then pulverized, thereby obtaining a granular solid composite oxide catalyst having uniform particle sizes between 0.85 mm and 1.4 mm.

Example 1

A stainless reaction tube having an internal diameter of 10.9 mm and a length of 300 mm was filled with 3.0 mL of the composite oxide catalyst produced in Production example 1. A stainless tube having an external diameter of 3.1 mm was inserted to the reaction tube, and a thermocouple was installed in the inserted tube to measure the temperature within the reactor. In addition, an electric furnace was used as a heating medium.

A mixed gas of nitrogen and oxygen mixed at 9:1 and water vapor were fed in advance at 446.4 mmol/hr and 153.4 mmol/hr, respectively, to a reactor, the temperature of which had been previously increased, a raw-material gas having a composition shown in Table 1 was fed at 74.8 mmol/hr to the reactor to perform oxidative dehydrogenation reaction. The mean temperature within the reactor was 350° C., and pressure was 0.0 MPa in terms of gauge pressure. Product gas coming out from the reactor outlet was sampled at 1 hour, 10 hours, and 14 hours after the initiation of the reaction and each sample was analyzed by gas chromatography (manufactured by Agilent Technologies, Model 6850A). As a result of analyses, conversion rates of straight-chain butene were as shown in Table 1.

The amount of energy required for heating the raw-material gas of Example 1 in the reactor was 1.05, based on the amount of energy, 1.00, required for heating raw materials excluding hydrocarbons having 5 or more carbon atoms (raw materials of butanes and butenes alone) in the reactor.

Example 2

Except for changing the composition of a raw-material gas to the relevant composition in Table 1, a reaction was carried out under the same conditions as in Example 1. Product gas was sampled at 1 hour and 10 hours after the initiation of the reaction, and samples were analyzed under the same conditions as in Example 1. As a result of analyses, the conversion rates of straight-chain butene were as shown in Table 1.

Note that, since pressure within the reactor increased to 0.1 MPa in terms of gauge pressure due to reactor blockage at 20 hours after the initiation of the reaction, the experiment was stopped.

The amount of energy required for heating the raw-material gas of Example 2 in the reactor was 1.00, based on the amount of energy, 1.00, required for heating raw materials excluding hydrocarbons having 5 or more carbon atoms (raw materials of butanes and butenes alone) in the reactor.

Example 3

Except for changing the composition of a raw-material gas to the relevant composition in Table 1, a reaction was carried out under the same conditions as in Example 1. Product gas was sampled at 1 hour, 10 hours, and 24 hours after the initiation of the reaction, and samples were analyzed under the same conditions as in Example 1. As a result of analyses, the conversion rates of straight-chain butene are as shown in Table 1.

The amount of energy required for heating the raw-material gas of Example 3 in the reactor was 1.00, based on the amount of energy, 1.00, required for heating raw materials excluding hydrocarbons having 5 or more carbon atoms (raw materials of butanes and butenes alone) in the reactor.

Example 4

Except for changing the composition of a raw-material gas to the relevant composition in Table 1, a reaction was carried out under the same conditions as in Example 1. Product gas was sampled at 1 hour, 10 hours, and 24 hours after the initiation of the reaction, and samples were analyzed under the same conditions as in Example 1. As a result of analyses, the conversion rates of straight-chain butene were as shown in Table 1.

The amount of energy required for heating the raw-material gas of Example 4 in the reactor was 1.05, based on the amount of energy, 1.00, required for heating raw materials excluding hydrocarbons having 5 or more carbon atoms (raw materials of butanes and butenes alone) in the reactor.

Example 5

Except for changing the composition of a raw-material gas to the relevant composition in Table 1, a reaction was carried out under the same conditions as in Example 1. Product gas was sampled at 1 hour, 10 hours, and 24 hours after the initiation of the reaction, and samples were analyzed under the same conditions as in Example 1. As a result of analyses, the conversion rates of straight-chain butene were as shown in Table 1.

The amount of energy required for heating the raw-material gas of Example 5 in the reactor was 1.05, based on the amount of energy, 1.00, required for heating raw materials excluding hydrocarbons having 5 or more carbon atoms (raw materials of butanes and butenes alone) in the reactor.

Comparative Example 1

Except for changing the composition of a raw-material gas to the relevant composition in Table 1, a reaction was carried out under the same conditions as in Example 1. Product gas was sampled at 1 hour after the initiation of the reaction, and sample was analyzed under the same conditions as in Example 1. As a result of analysis, the conversion rate of straight-chain butene was as shown in Table 1.

Note that, since pressure within the reactor increased to 0.1 MPa in terms of gauge pressure due to reactor blockage at 7 hours after the initiation of the reaction, the experiment was stopped.

Comparative Example 2

Except for changing the composition of a raw-material gas to the relevant composition in Table 1, a reaction was carried out under the same conditions as in Example 1. Product gas was sampled at 1 hour, 10 hours, and 24 hours after the initiation of the reaction, and samples were analyzed under the same conditions as in Example 1. As a result of analyses, the conversion rates of straight-chain butene were as shown in Table 1.

The amount of energy required for heating the raw-material gas of Comparative Example 2 in the reactor was 1.10, based on the amount of energy, 1.00, required for heating raw materials excluding hydrocarbons having 5 or more carbon atoms (raw materials of butanes and butenes alone) in the reactor.

TABLE 1

|  |  | Example 1 | Example 2 | Example 3 | Example 4 | Example 5 | Comparative Example 1 | Comparative Example 2 |
|---|---|---|---|---|---|---|---|---|
| Raw-material gas composition (mol %) | Butanes | 22.7 | 23.9 | 23.8 | 22.7 | 22.7 | 24 | 21.6 |
|  | Butenes | 72.3 | 76 | 75.9 | 72.3 | 72.3 | 76 | 68.4 |
|  | C5 | 5 | 0.1 | 0.3 | 0 | 0 | 0 | 0 |
|  | C6 | 0 | 0 | 0 | 5 | 0 | 0 | 0 |
|  | C14 | 0 | 0 | 0 | 0 | 2 | 0 | 10 |
|  | C20 | 0 | 0 | 0 | 0 | 3 | 0 | 0 |
| Butene conversion rate (mol %) | 1 hour later | 25 | 25.9 | 25.8 | 25.2 | 25.4 | 26.3 | 24.2 |
|  | 10 hours later | 24.9 | 25.6 | 25.4 | 24.9 | 24.6 | — | 24 |
|  | 24 hours later | 24.6 | — | 25.6 | 25 | 24.7 | — | 24.1 |
| Required energy (relative value) |  | 1.05 | 1 | 1 | 1.05 | 1.05 | 1 | 1.1 |

The invention claimed is:

1. A method for producing butadiene, comprising:

providing a raw material gas comprising straight-chain butene and an oxygen-containing gas comprising molecular oxygen, adding hydrocarbons having 5 or more carbon atoms to the raw material gas or adjusting the amount of hydrocarbons having 5 or more carbon atoms in the raw material gas to obtain an amount of hydrocarbons having 5 or more carbons atoms in the raw material gas in the range of 0.2-7.0 mol %, and performing oxidative dehydrogenation reaction of the raw material gas with the oxygen-containing gas in a reactor and in the presence of a catalyst to produce a product gas comprising butadiene, wherein:

the catalyst comprises a composite oxide containing molybdenum and bismuth;

the concentration of isobutene in the raw material gas is 1.0 mol % or less;

the concentration of butadiene in the raw material gas is 1.0 mol % or less; and the amount of hydrocarbons having 5 or more carbon atoms in the raw material gas allows dissolving byproducts of the oxidative dehydrogenation reaction and prevents reactor blockage.

2. The method according to claim 1, wherein the amount of hydrocarbons having 5 or more carbon atoms in the raw-material gas is in the range of 0.2-6.0 mol %.

3. The method according to claim 1, wherein the concentration of the straight-chain butene in the raw-material gas is 60 mol % or more.

* * * * *